United States Patent [19]

Alliger

[11] 4,330,531
[45] May 18, 1982

[54] GERM-KILLING MATERIALS

[76] Inventor: Howard Alliger, 10 Ponderosa Dr., Melville, N.Y. 11476

[21] Appl. No.: 161,336

[22] Filed: Jun. 20, 1980

Related U.S. Application Data

[63] Continuation of Ser. No. 896,724, Apr. 17, 1978, abandoned, which is a continuation-in-part of Ser. No. 670,674, Mar. 26, 1976, Pat. No. 4,084,747.

[51] Int. Cl.³ .................. A61K 33/20; A61K 7/20
[52] U.S. Cl. .................................. 424/149; 424/53
[58] Field of Search .............. 424/43, 44, 49–58, 424/149, 362; 252/107, 187; 222/3

[56] References Cited

U.S. PATENT DOCUMENTS

| | | | |
|---|---|---|---|
| 2,484,637 | 10/1949 | Mattocks et al. | 424/362 |
| 2,550,622 | 4/1951 | Taub | 424/362 |
| 2,623,840 | 12/1952 | Taub | 424/362 |
| 2,701,782 | 2/1955 | Culter | 424/362 |
| 2,726,982 | 12/1955 | Ochs | 424/362 |
| 3,663,716 | 5/1972 | Stolar | 424/343 |
| 3,843,548 | 10/1974 | James | 424/149 |
| 3,920,835 | 11/1975 | Van Scott et al. | 424/311 |
| 4,084,747 | 4/1978 | Alliger | 239/4 |
| 4,104,190 | 8/1978 | Hartshorn | 424/149 |

FOREIGN PATENT DOCUMENTS 955848 10/1974 Canada.
2343171 3/1975 Fed. Rep. of Germany.

OTHER PUBLICATIONS

Chem. Abstracts 82 #173182G (1975) of Milanato Ger. Offen. 2343171, Mar. 6, 1975, 14 pages.

*Primary Examiner*—Shep K. Rose
*Attorney, Agent, or Firm*—Hopgood, Calimafde, Kalil, Blaustein & Judlowe

[57] ABSTRACT

There is disclosed a germ-killing gel, a germ-killing soap, a germ-killing toothpaste and applicators for dispensing germ-killing compositions. These compositions include a first material containing sodium chlorite and a second material containing lactic acid in sufficient amount to lower the pH of the aqueous media to less than about seven.

5 Claims, 13 Drawing Figures

GERM-KILLING MATERIALS

REFERENCE TO RELATED APPLICATION

This application is a continuation of Ser. No. 896,724, filed Apr. 17, 1978 and entitled "Germ Killing Materials" which is a continuation-in-part of application Ser. No. 670,674, filed Mar. 26, 1976, for "Germ-Killing Composition and Method" now U.S. Pat. No. 4,084,747.

BACKGROUND OF THE INVENTION

1. Field of the Invention

This invention relates to germ-killing materials and more particularly to materials adapted for use in cleaning, sanitizing, deodorizing, and disinfecting surfaces into or onto which the material is to be applied.

2. Description of the Prior Art

Chlorine dioxide ($ClO_2$) has been tried in the past for skin disinfection with limited success. One such chlorine dioxide preparation was called Cryoclave, produced by International Dioxide. Chlorine dioxide has, however, had more success as an additive to medicine to inhibit microbial growth in the medicine itself, as disclosed in Canadian Pat. No. 955,848, than for its antimicrobial activity on the body.

The usual method for using or incorporating chlorine dioxide gas has been to dissolve the gas in a liquid to form a solution. This method has a number of drawbacks. The chlorine dioxide gas tends to release from the solution so that its shelf-life is relatively short compared to other skin medications. When the product is applied to the skin as a liquid, the lack of adherence of the product to the skin or lesion results in a short contact time. Since fungus diseases and other types of infected lesions usually require many hours or even days of contact, a strict regimen of reapplication would be necessary to ensure adequate therapeutic response.

These objections to the use of chlorine dioxide on the skin can be overcome or substantially alleviated if the gas is incorporated in a gel base. The high viscosity of these gels and their bioadhesion to the skin prevents escape of the gas and also holds the gas in contact with the skin for long periods, particularly in conjunction with the use of a conventional occlusive barrier, such as a plastic film bandage for the afflicted area.

The process of acidifying sodium chlorite to produce chlorine dioxide within the gel is novel. The gelling material must not only be compatible with the strong oxidizing action of chlorine dioxide, so that there is no complexing with this reactive substance, but must also be compatible with the alkaline sodium chlorite and the acid. Many substances are not compatible with chlorine dioxide. Most flavors and coloring agents, for example, will react with chlorine dioxide. Canadian Pat. No. 955,848 discloses adding these kinds of substances, but this addition reduces the germicidal effectiveness of the chlorine dioxide and thus shortens the shelf-like of the product. A further example of incompatibility is hydrogen peroxide, which has been successfully gelled with a glycerin base. Glycerin, however, will react with chlorine dioxide and therefore cannot be used as a "thickener" for a base with chlorine dioxide producing components. The gelling agent must, of course, be non-toxic, non-irritating, and easily removed from the skin.

SUMMARY OF THE INVENTION

Thus, the primary object of the present invention is to provide improved cleaning, deodorizing, sanitizing, and disinfecting materials including gels, soap products, toothpaste, and the like, each packaged with one material containing sodium chlorite separate from another material containing lactic acid in sufficient amount to lower the pH of the final product formed upon mixing of the materials to less than about 7.

DETAILED DESCRIPTION OF THE INVENTION

Figure 1:
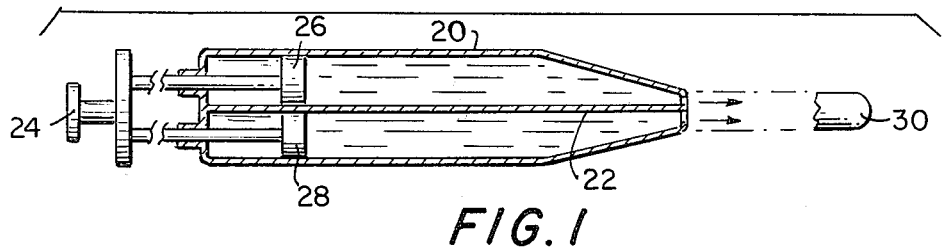
FIG. 1 is a longitudinal sectional view of a dual syringe used in dispensing the germ-killing product.

The present invention is further illustrated by the following examples. All parts and percentages in the examples as well as in the specification and claims are by weight unless otherwise specified.

EXAMPLE I

This example illustrates the production of a gel mixed in situ. This gel is most effective in the treatment of burns and is efficasious in killing germs on all surfaces. It is particularly useful for the treatment of acne.

| GEL | | | |
|---|---|---|---|
| | PART A | | |
| Thickener | METHYL CELLULOSE (High Viscosity, 4,000 CPS) | 8.0% | W/W |
| Preservative | BENZYL ALCOHOL | 5.0% | W/W |
| | WATER | 85.7% | W/W |
| | LACTIC ACID | 1.3% | W/W |
| | PART B | | |
| | METHYL CELLULOSE (High Viscosity, 4,000 CPS) | 8.0% | W/W |
| | BENZYL ALCOHOL | 5.0% | W/W |
| | WATER | 86.8% | W/W |
| | SODIUM CHLORITE | 0.2% | W/W |

Procedure for Part A: Heat one-half of the 85.7% water to boiling and add methyl cellulose with constant agitation. Add the balance of the water as "ice water" (i.e., about 5° C.) containing the benzyl alcohol and the lactic acid. Stir initially to blend the ingredients, then allow them to cool to room temperature with occasional stirring until the composition gels.

Procedure for Part B: Same as for Part A, except substitute sodium chlorite for lactic acid.

Package parts A and B in separate tubes with directions to mix equal parts before use.

EXAMPLE II

This example illustrates a soap product which employs lactic acid and sodium chlorite.

STRIPED SOAP BAR

| | | | |
|---|---|---|---|
| Detergent | IGEPON AC-78 (83% solids)[1] | 58% | W/W |
| Preservative | VANCIDE 89 RE[2] | 1% | W/W |
| Thickener | VEEGUM F[2] | 1% | W/W |
| Emollient | CETYL ALCOHOL | 2% | W/W |
| Emulsifier | GLYCERYL MONOSTEARATE A.S. | 6% | W/W |
| Emulsifier | STEARYL ALCOHOL | 7% | W/W |
| Emollient | MODULAN[3] | 3% | W/W |
| Humectant | POLYETHYLENE GLYCOL 6000 | 13% | W/W |
| | WATER | 9% | W/W |

[1] commercially available from GAF Corporation, New York, N.Y.
[2] commercially available from the R. T. Vanderbilt Co., New York, N.Y.
[3] commercially available from the American Cholesterol Products, Inc., Edison, N.J.

Procedure: Add the VANCIDE 89RE and the VEEGUM F to a part of the IGEPON AC-78, then add the rest of the IGEPON AC-78 with thorough blending. Heat a mixture of the remaining ingredients to 75° C. Add the IGEPON mixture to the remaining ingredients with agitation until uniform. Divide the mixture into two parts, A and B. To Part A, add 1% W/W sodium chlorite, and to part B add 6% W/W lactic acid plus 1% W/W Tartrazine Dye (F, D. & C.). Allow Parts A and B to cool to room temperature and gently blend the two parts to produce swirls of the yellow Part B in the white Part A. Press the mixture into bars or cakes.

EXAMPLE III

This invention may also be used in producing a toothpaste as described hereinbelow:

STRIPED TOOTHPASTE

| | | | |
|---|---|---|---|
| Thickener | VEEGUM F | 1.25% | W/W |
| Thickener | METHYL CELLULOSE (Med. Viscosity, 400 CPS) | 0.70% | W/W |
| | WATER | 24.00% | W/W |
| Humectant | SORBITOL (70% AQUEOUS SOLUTION) | 25.00% | W/W |
| Abrasive | DICALCIUM PHOSPHATE DIHYDRATE | 45.00% | W/W |
| | MINT FLAVOR | 1.00% | W/W |
| Detergent | SODIUM LAURYL SULFATE | 1.50% | W/W |
| Preservative | METHYL PARABEN | 0.25% | W/W |
| | LACTIC ACID | 1.30% | W/W |

All of the Thickener may be METHYL CELLULOSE.

Procedure: Dry blend the VEEGUM F and Methyl Cellulose. Add this blend to the water (heated to 70° C.) slowly, agitating continuously until uniform and cooled to room temperature. Add the SORBITOL solution and DICALCIUM PHOSPHATE DIHYDRATE in alternate portions to the VEEGUM F/Methyl Cellulose mixture until smooth. Then add the LACTIC ACID, MINT FLAVOR, METHYL PARABEN and SODIUM LAURYL SULFATE in order, blending each thoroughly (use gentle agitation) with the SODIUM LAURYL SULFATE to avoid incorporation of air.

In a separate operation, prepare the following GEL:

| | | | |
|---|---|---|---|
| Thickener | METHYL CELLULOSE (High Viscosity, 4000 CPS) | 8.0% | W/W |
| Preservative | BENZYL ALCOHOL | 5.0% | W/W |
| Color | ERYTHROSIN J (F. S. & C.) | 1.0% | W/W |
| | WATER | 85.8% | W/W |
| | SODIUM CHLORITE | 0.2% | W/W |

Procedure: Heat one-half of the water to boiling and add METHYL CELLULOSE with constant agitation. Add the balance of the water as "ice water" (about 5° C.), containing BENZYL ALCOHOL, ERYTHROSIN J (cherry-red dye) and SODIUM CHLORITE. Stir initially to blend the ingredients, then allow the blend to cool to room temperature with occasional stirring until gelled.

Package the white toothpaste and the red gel in plastic tubes with separate compartments for each component, but with adjacent extrusion orifices (the toothpaste as a single stream; for the gel several small orifices should be arranged around the periphery of the toothpaste orifice so that a striped effect is produced upon extrusion). Such tubes are commercially available.

The following description refers to the accompanying drawings wherein like reference numerals designate similar parts throughout the various views.

In FIG. 1 there is shown a dual syringe especially adapted for use in dispensing solutions or gels and contains a syringe housing 20 provided with a separator 22 therein. A single actuator 24 controls dual plungers 26 and 28 which expel the contents from the housing 20 simultaneously and in equal amounts as indicated at 30 into a material ready to be evenly spread on the surface to be treated.

Figure 2:
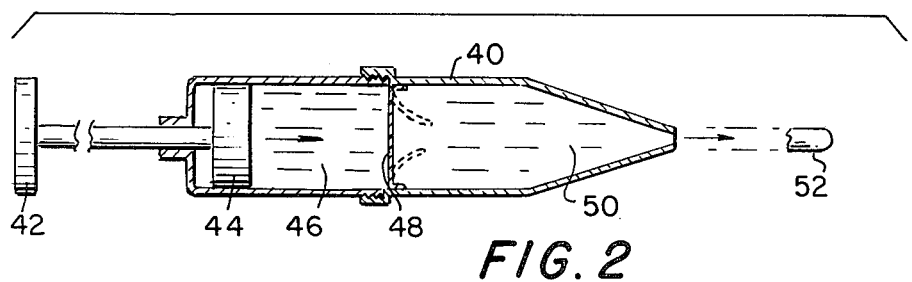
FIG. 2 is a longitudinal sectional view of a single syringe having dual compartments.

In FIG. 2 there is shown a syringe housing 40 having a single actuator 42 controlling a single plunger 44 which, when actuated, causes the material 46 to break through the frangible barrier 48 and mix with the material 50 so that the combination of ingredients can be expelled as composite gel 52 which is ready for use.

Figure 3:
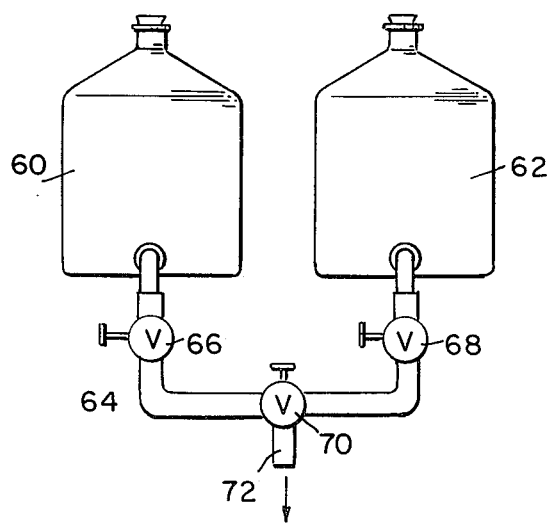
FIG. 3 is a schematic diagram illustrating a dual reservoir applicator.

In FIG. 3 there is shown two reservoirs 60 and 62 interconnected by tubing 64 with separate control valves 66 and 68 provided together with a shut-off valve 70 for controlling fluid flow in the direction of arrow 72.

Figure 4:
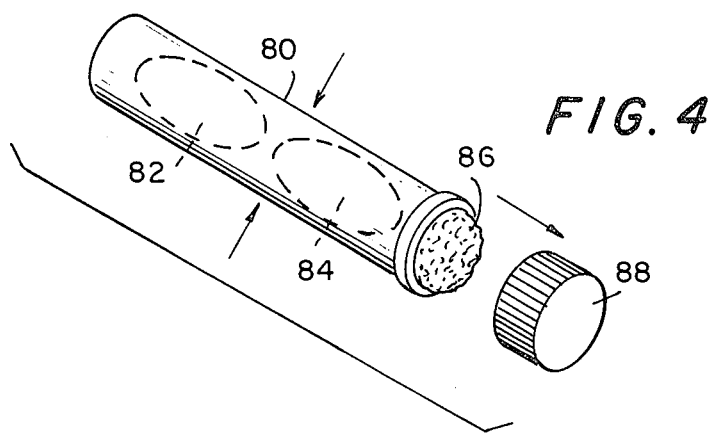
FIG. 4 is an exploded perspective view showing a squeezable vial.

In FIG. 4 there is shown a squeezable vial 80 containing frangible containers 82 and 84 which will break upon application of pressure to the vial permitting the ingredients to admix and be delivered through the cotton dauber 86 in a convenient manner.

Figure 5:
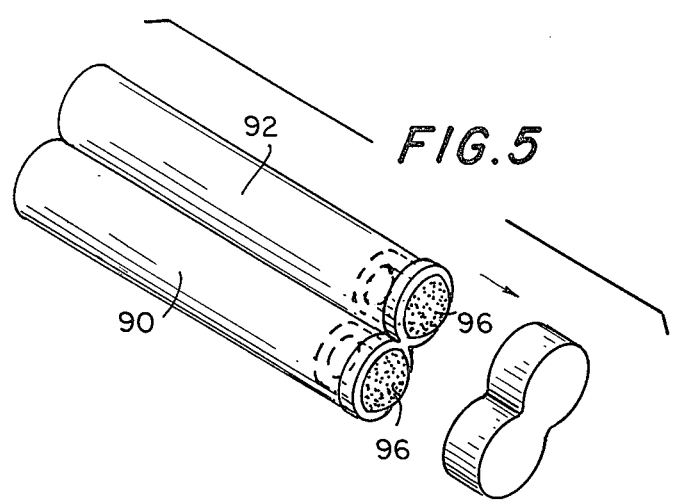
FIG. 5 is an exploded perspective view of a rigid double dispenser.

In FIG. 5 there is shown a dual applicator including two containers 90 and 92 filled with the two different materials and each having a sponge applicator head 94 and 96 for simultaneously applying the various materials. The two containers 90 and 92 are bonded or otherwise joined together.

Figure 6:
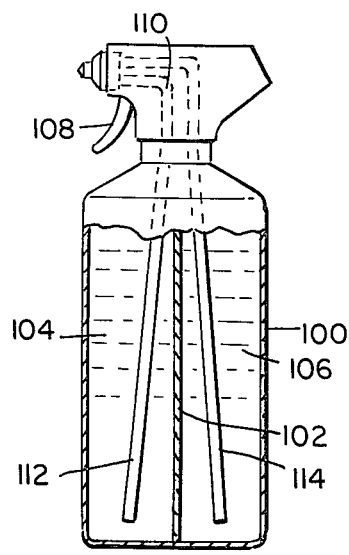
FIG. 6 is a sectional detail view of a trigger-type dual dispenser.

In FIG. 6 there is shown a trigger-actuated dispenser in which a container 100 is provided with a divider 102 for maintaining the solutions 104 and 106 separate. When the trigger 108 of the conventional pump actuator 110 is depressed, material is sucked through each of the tubes 112 and 114 and simultaneously sprayed.

Figure 7:
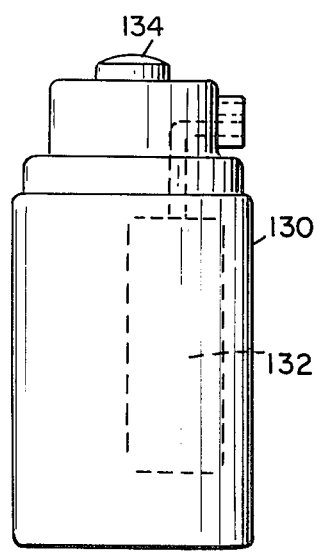
FIG. 7 is a schematic view showing a dual dispenser.

In FIG. 7 there is shown a dual dispenser similar to the foam shaving cream dispenser marketed by The Gilette Company in which the outer container 130 contains a first material while an inner container 132 contains the second material. Both are under gas pressure and when the actuator 134 is depressed, both materials are simultaneously dispensed through as a result of the gaseous pressure.

Figure 8:
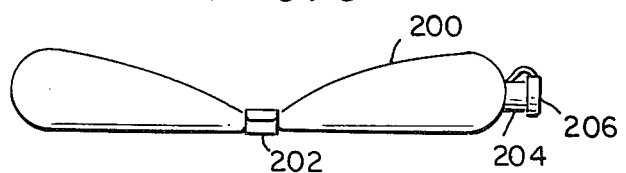
FIG. 8 is an elevational view of a dual dispensing plastic pack having a removable separator.
Figure 9:
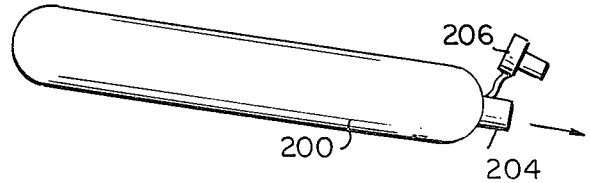
FIG. 9 is a view of the dispenser shown in FIG. 8 with a separator removed therefrom.

Referring now to FIGS. 8 and 9, there is shown a plastic container 200 which is first partially filled with one solution after which a removable separator 202 is applied. Thereafter, the other section is filled through the neck 204 and the cap 206 secured in place. When it is desired to use the contents, the separator is removed and, as shown in FIG. 9, the entire contents are mixed and ready for application.

Figure 10:
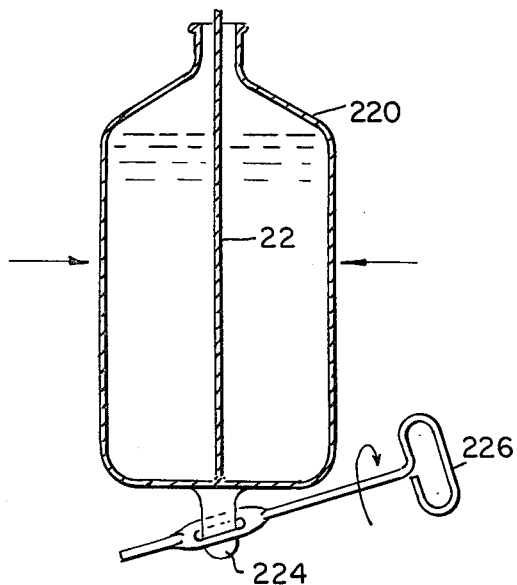
FIG. 10 is a sectional detail view of a squeeze bottle having a center separator.

In FIG. 10 there is shown a tube or container 220 including a separator 22. A tab 224 is provided for which a wind-up key 226 can be used to expel the contents of the container 220 in equal proportions.

Figure 11:
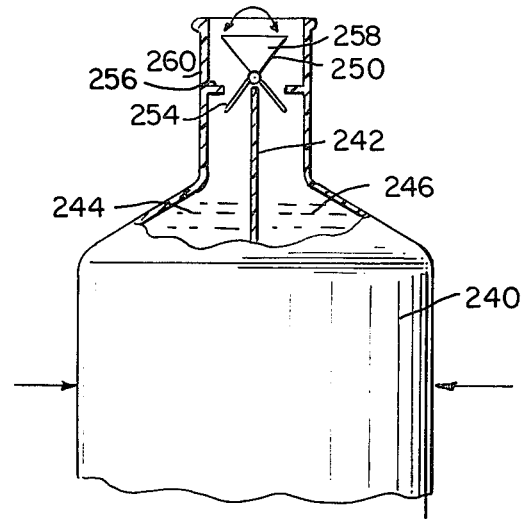
FIG. 11 is a sectional detail view illustrating means used in a dispenser for preventing unequal dispensing of materials.

Referring now to FIG. 11, there is shown a container 240 having a divider 242 therein. The container 240 is adapted to contain two different gels 244 and 246 and movement of the gel 244 without corresponding movement of the gel 246 or vice versa through its channel without the other gel moving will actuate a pivotal valve member 250 to prevent passage of the other gel. For example, if gel 244 was being dispensed and gel 246 was not, the vane 254 would be moved into a valve closed engagement with its valve seat 256 while valve head 258 would contact the neck portion 260 of the container to prevent fluid flow of the gel 246. Even flow of both gels will by-pass the vane and cause equal delivery.

Figure 12:
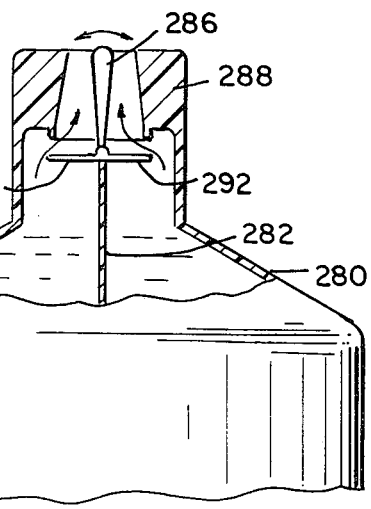
FIG. 12 is a sectional detail view illustrating a modified form of the means controlling the amounts of fluid flow.

FIG. 12 shows another form of container 280 containing a separator 282 as well as a guide 286 at the neck 288 of the container 280 and is so arranged that the guide 286 will lock on the movement of only one of the gels within the container so as to cause one of the valve vanes 290 and 292 to prevent further movement until the delivery of both gels has been equalized.

Figure 13:
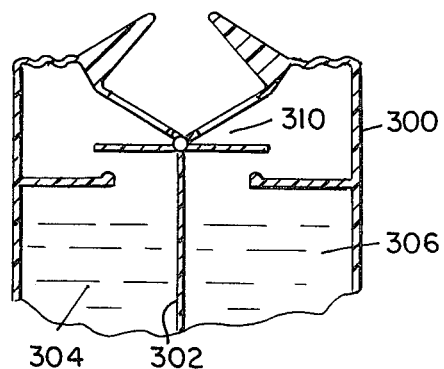
FIG. 13 is a sectional detail view of yet another dispenser control means.

In FIG. 13 there is shown an additional modified form of the invention in which the container 300 has a divider 302 therein for separating the compartments 304 and 306 containing different gels from each other. Pivoted to the divider 302 is a valve assembly 310 which includes means for preventing unequal flow of the separate gels.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

What is claimed is:

1. In a germ-killing skin medication adapted for treatment of skin diseases such as acne and burns comprising two gels adapted to be simultaneously applied and mixed in situ and to adhere on the skin or lesion surface to be treated, including the treatment of burns as well as acne, the improvement comprising said first get being an aqueous gel comprising sodium chlorite and said second gel being an aqueous gel comprising lactic acid, there being sufficient of said lactic acid to lower the pH of said medication to less than about 7.

2. The medication of claim 1, wherein said first gel includes 0.2% by weight sodium chlorite and said second gel includes 1.3% by weight lactic acid.

3. The medication of claim 2, wherein said first gel and said second gel each include approximately 8% methyl cellulose by weight and approximately 5% benzyl alcohol by weight.

4. The medication of claim 1, wherein said first and second gels each contains a thickener and a preservative.

5. The medication of claim 4, wherein said thickener is methyl cellulose and said preservative is benzyl alcohol.

* * * * *